(12) United States Patent
Fort

(10) Patent No.: US 10,397,715 B2
(45) Date of Patent: Aug. 27, 2019

(54) SYSTEM AND METHOD FOR IMPROVING DATA INTEGRITY AND POWER EFFICIENCY

(71) Applicant: Cochlear Limited, Macquarie University, NSW (AU)

(72) Inventor: Andrew D. Fort, Leuven (BE)

(73) Assignee: Cochlear Limited, Macquarie University, NSW (AU)

( * ) Notice: Subject to any disclaimer, the term of this patent is extended or adjusted under 35 U.S.C. 154(b) by 1 day.

(21) Appl. No.: 15/967,938

(22) Filed: May 1, 2018

(65) Prior Publication Data

US 2018/0249264 A1  Aug. 30, 2018

Related U.S. Application Data

(63) Continuation of application No. 14/317,111, filed on Jun. 27, 2014, now Pat. No. 9,986,350.

(51) Int. Cl.
*A61N 1/05* (2006.01)
*A61N 1/36* (2006.01)
*A61N 1/372* (2006.01)
*H04R 25/00* (2006.01)

(52) U.S. Cl.
CPC ......... *H04R 25/70* (2013.01); *A61N 1/36036* (2017.08); *A61N 1/37276* (2013.01); *A61N 1/0541* (2013.01); *H04R 2225/67* (2013.01)

(58) Field of Classification Search
CPC .. H04R 25/70; H04R 25/606; A61N 1/36032; A61N 1/37252
USPC ........................................................ 381/314
See application file for complete search history.

(56) References Cited

U.S. PATENT DOCUMENTS

| 7,623,827 B2 | 11/2009 | Ibrahim |
| 2001/0033267 A1 | 10/2001 | Kim et al. |
| 2005/0085873 A1* | 4/2005 | Gord ............... A61N 1/372 607/61 |
| 2006/0268643 A1 | 11/2006 | Schreck et al. |
| 2008/0195177 A1 | 8/2008 | Ibrahim |
| 2008/0234784 A1* | 9/2008 | Li ............... A61N 1/37223 607/60 |
| 2009/0080349 A1 | 3/2009 | Rofougaran |
| 2010/0269007 A1 | 10/2010 | Laviolette et al. |

(Continued)

FOREIGN PATENT DOCUMENTS

| JP | 2007067786 A | 3/2007 |
| WO | 2013084211 A1 | 6/2013 |

*Primary Examiner* — Sean H Nguyen
(74) *Attorney, Agent, or Firm* — Edell, Shapiro & Finnan, LLC

(57) ABSTRACT

A method performed by a device includes generating a first signal in accordance with a first set of one or more operational settings, and determining whether the signal has an acceptable data integrity. If the device determines that the signal has an acceptable data integrity, the method includes maintaining a configuration of the device with the first set of one or more operational settings. If the device determines that the signal does not have an acceptable data integrity, then the method includes automatically configuring the device with a second set of one or more operational settings. The configuration of the device ith the first set of one or more operational settings is associated with greater power efficiency than the configuration of the device with the second set of one or more operational settings.

29 Claims, 4 Drawing Sheets

(56) References Cited

U.S. PATENT DOCUMENTS

2011/0176060 A1 7/2011 Lee et al.
2012/0213394 A1 8/2012 Fort et al.
2014/0025137 A1 1/2014 Meskens

* cited by examiner

SYSTEM AND METHOD FOR IMPROVING DATA INTEGRITY AND POWER EFFICIENCY

CROSS REFERENCE TO RELATED APPLICATION

The present application is a continuation application of U.S. patent application Ser. No. 14/317,111, filed on Jun. 27, 2014, the entire contents of which is incorporated by reference herein.

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, and/or the bones of the middle ear. Sensorineural hearing loss typically results from a dysfunction in the inner ear, such as in the cochlea where sound or acoustic vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sound into the person's ear. Vibration-based hearing devices typically include a small microphone to detect sound and a vibration mechanism to apply vibrations, which represent the detected sound, directly or indirectly to a person's bone or teeth, thereby causing vibrations in the person's inner ear and bypassing the person's auditory canal and middle ear.

Vibration-based hearing devices include, for example, bone conduction devices, direct acoustic cochlear stimulation devices, and other vibration-based devices. A bone conduction device typically utilizes a surgically implanted mechanism or a passive connection through the skin or teeth to transmit vibrations via the skull. Similarly, a direct acoustic cochlear stimulation device typically utilizes a surgically implanted mechanism to transmit vibrations, but bypasses the skull and more directly stimulates the inner ear. Other vibration-based hearing devices may use similar vibration mechanisms to transmit acoustic signals via direct or indirect vibration applied to teeth or other cranial or facial structures.

Persons with certain forms of sensorineural hearing loss may benefit from implanted prostheses, such as cochlear implants and/or auditory brainstem implants. Generally, cochlear implants and auditory brainstem implants electrically stimulate auditory nerves in the cochlea or the brainstem to enable persons with sensorineural hearing loss to perceive sound. For example, a cochlear implant uses a small microphone to convert sound into a series of electrical signals, and uses the series of electrical signals to stimulate the auditory nerve of the recipient via an array of electrodes implanted in the cochlea. An auditory brainstem implant can use technology similar to cochlear implants, but instead of applying electrical stimulation to a person's cochlea, the auditory brainstem implant applies electrical stimulation directly to a person's brainstem, bypassing the cochlea altogether.

In addition, some persons may benefit from a bimodal hearing prosthesis that combines one or more characteristics of acoustic hearing aids, vibration-based hearing devices, cochlear implants, or auditory brainstem implants to enable the person to perceive sound.

OVERVIEW

The present disclosure relates to configuring a system or device, such as a hearing prosthesis. More particularly, the disclosure relates to selecting a set of one or more operational settings or parameters for the device to help optimize or improve power efficiency and data integrity. An example of such a hearing prosthesis includes an implantable component that, in one example, is at least partially implanted in a recipient, and is configured to apply stimulation to the recipient to allow the recipient to perceive sound. The hearing prosthesis can also include an external component that, in one example, is used to convert external audible sounds into electrical signals, which include audio data that represents the audible sounds. The external component transmits the electrical signals to the implantable component. The electrical signals can be transmitted, for instance, over a radio frequency (RF) link established between respective coils of the implantable and external components. The implantable component can then apply the electronic signals to an actuator, such as an electrode array implanted in the recipient's cochlea, to stimulate the recipient's hearing system and allow the recipient to perceive the audio data as sound.

In a hearing prosthesis, good data integrity of the transmitted electrical signals is important for proper operation of the device so that the audible data can be accurately and consistently perceived as sound when the electrical signals are applied to the actuator. In practice, obtaining good data integrity can be achieved by implementing a combination or set of one or more data integrity strategies or settings. These settings can include, for example, quality factor (Q) control mechanisms (such as, coupling dampening coils and/or resistors), driver settings used to transmit the electronic signals, dynamic cycle modification (DCM) tables that are used to modify the electronic signals, power tokens that can be added to the electronic signals, data detection thresholds, and others. Commonly, hearing prostheses may be configured to apply a single combination of settings that optimizes data integrity for an entire population of recipients.

However, there may also be various recipient-specific factors that affect the implementation of settings for obtaining good data integrity. These factors include, for example, skin flap thickness (SFT), electronic tolerances (such as, compliance voltage and electrode impedance), stimulation settings, and others. Further, such factors may not be known until after the device is implanted in the recipient. Consequently, when a single combination of settings is applied to optimize data integrity for an entire population, not all of the applied device settings may help to obtain good data integrity for a particular recipient.

In addition, the device settings that are used to provide good data integrity can be lossy schemes that reduce power efficiency of the device. Such lossy device settings include dampening features and Q control mechanisms, for example. As a result, when a single combination of settings is applied for an entire population, one or more of the applied device settings may not be necessary to obtain good data integrity for a given user, and may reduce power efficiency of the device. For instance, dampening features may be used to obtain good data integrity for a recipient with a low SFT, but may not be necessary for a recipient with a high SFT. Thus, applying the dampening features for a recipient with a high SFT may not be necessary to obtain good data integrity and may reduce power efficiency.

In accordance with the present disclosure, different combinations of one or more device settings can be applied and tested to determine whether the device settings provide good data integrity. Generally, different combinations of device settings can be ordered from more power efficient to less power efficient. The combinations of device settings can then be tested one at a time starting from a relatively higher power efficiency setting to relatively lesser power efficiency settings. This testing approach can facilitate the identification of the most power efficient combination of device settings that also provides good data integrity.

In one aspect, an external component of a hearing prosthesis is configured to apply a combination of device settings, to generate an electronic signal by operating in accordance with the applied combination, and to transmit the electronic signal to an implanted component of the hearing prosthesis. The applied combination of device settings can be associated with a potential greatest power efficiency (or in any event, a relatively high power efficiency), as compared with power efficiencies associated with other combinations of device settings. In one example, if the implanted component then responds with another electronic signal that indicates that the transmitted electronic signal has good data integrity, the hearing prosthesis may responsively set itself to use the applied combination of device settings during subsequent operation thereof.

On the other hand, if the implanted component does not respond (or responds with another electronic signal that indicates that the transmitted electronic signal does not have good data integrity), the external component may then responsively apply a different set of device settings. The external and internal components can then repeat this process of generating an electronic signal (using a new set of device settings), transmitting the electronic signal, responding (or not responding) with another electronic signal indicative of the data integrity of the generated and transmitted electronic signal, and applying a new combination of device settings, as appropriate. When the external component applies a different combination of device settings, the external component can select and apply the different combination of device settings that is perhaps equally power efficient or less power efficient than the previously applied combination. In this way, the hearing prosthesis can select a combination of device settings that optimizes power efficiency while obtaining good data integrity.

In a further respect, this process can be implemented as program instructions, which may be loaded on a new device or added (e.g., with a firmware upgrade) to an existing device.

DETAILED DESCRIPTION

The following detailed description sets forth various features and functions of the disclosed embodiments with reference to the accompanying figures. In the figures, similar reference numbers typically identify similar components, unless context dictates otherwise. The illustrative embodiments described herein are not meant to be limiting. Aspects of the disclosed embodiments can be arranged and combined in a variety of different configurations, all of which are contemplated by the present disclosure. For illustration purposes, some features and functions are described with respect to medical devices, such as hearing prostheses. However, the features and functions disclosed herein may also be applicable to other types of devices, including other types of medical and non-medical devices.

Figure 1:
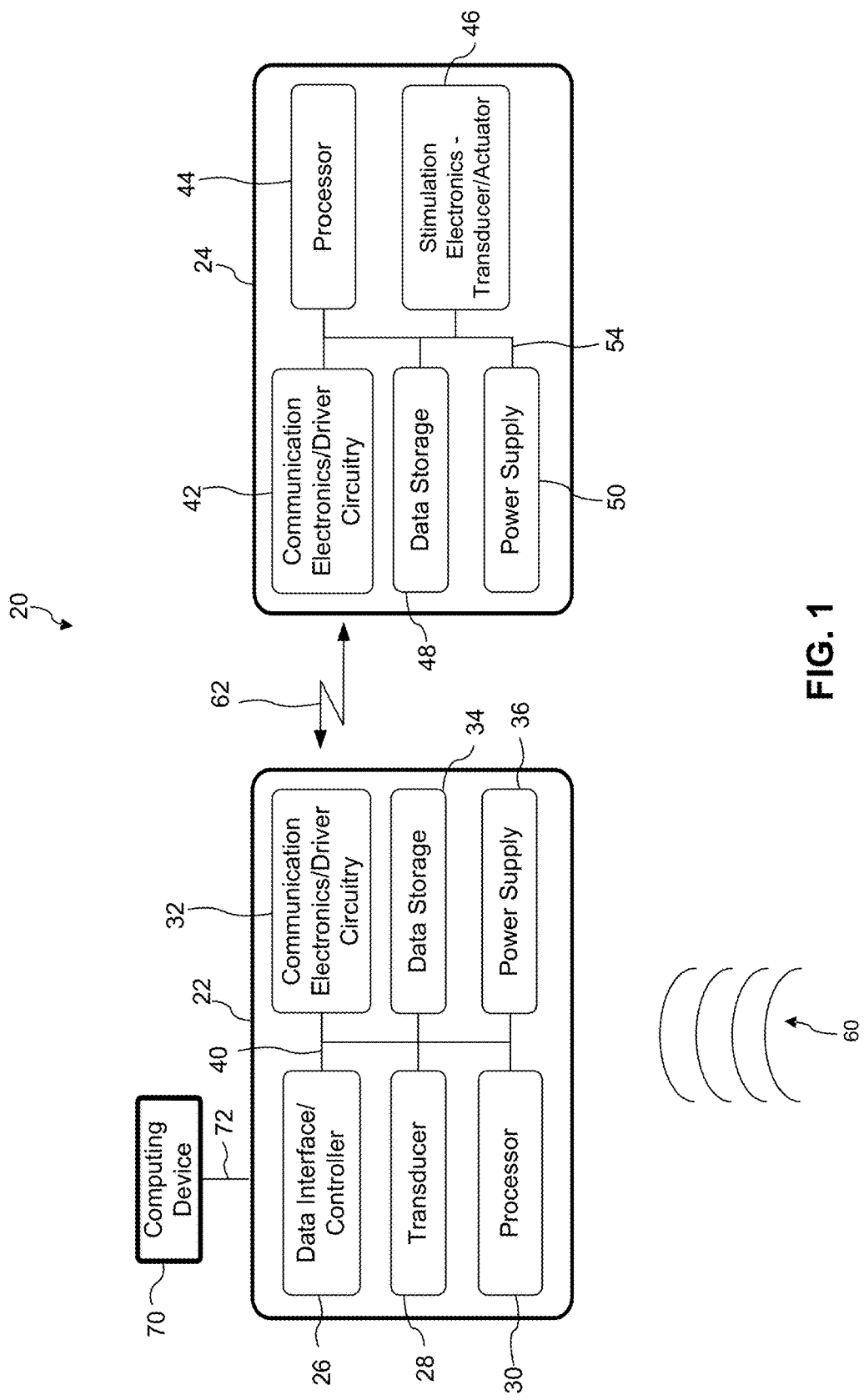
FIG. 1 is a block diagram of a device according to an embodiment of the present disclosure.

Referring now to FIG. 1, an example electronic device 20 includes a first component 22 and a second component 24. The device 20 can be a hearing prosthesis, such as a cochlear implant, an acoustic hearing aid, a bone conduction device, a direct acoustic cochlear stimulation device, an auditory brainstem implant, a bimodal hearing prosthesis, or any other type of hearing prosthesis configured to assist a prosthesis recipient to perceive sound. In this context, the first component 22 can be generally external to a recipient and communicate with the second component 24, which can be implanted in the recipient. In other examples, the components 22, 24 can both be at least partially implanted or can both be at least partially external to the recipient. Generally, an implantable component or device can be hermetically sealed and otherwise adapted to be at least partially implanted in a person.

In FIG. 1, the first component 22 includes a data interface or controller 26 (such as a universal serial bus (USB) controller), one or more transducers 28, a processor 30 (such as digital signal processor (DSP)), communication electronics 32 (such as an electromagnetic radio frequency (RF) transceiver), data storage 34, and a power supply 36, all of which are illustrated as being coupled directly or indirectly via a wired conductor or wireless link 40. In the example of FIG. 1, the second component 24 includes communication electronics 42 (such as another RF transceiver), a processor 44, stimulation electronics 46, data storage 48, and a power supply 50, all of which are illustrated as being coupled directly or indirectly via a wired conductor or wireless link 54.

The transducer 28 may include a microphone that is configured to receive external audible sounds 60. Further, the microphone may include combinations of one or more omnidirectional or directional microphones that are configured to receive background sounds and/or to focus on sounds from a specific direction, such as generally in front of the prosthesis recipient. Alternatively or in addition, the transducer 28 may include telecoils or other sound transducing components that receive sound and convert the received sound to electronic signals. Further, the device 20 may be configured to receive sound information from other sources, such as electronic sound information received through the data interface 26 of the first component 22 or from the communication electronics 42 of the second component 24.

In one example, the processor 30 of the first component 22 is configured to convert or encode the audible sounds 60 (or other electronic sound information) into encoded electronic signals that include audio data that represents sound information, and to apply the encoded electronic signals to the communication electronics 32. In the present example, the communication electronics 32 of the first component 22 are configured to transmit the encoded electronic signals as electronic output signals 62 to the communication electronics 42 of the second component 24. Illustratively, the communication electronics 32, 42 can include magnetically coupled coils that establish an RF link between the units 22, 24. Accordingly, the communication electronics 32 can transmit the output signals 62 encoded in a varying or alternating magnetic field over the RF link between the components 22, 24.

Generally, the communication electronics 32, 42 can include an RF inductive transceiver system or circuit. Such a transceiver system may further include an RF modulator, a transmitting/receiving/transceiver coil, and associated driver circuitry for driving the coil to radiate the output signals 62 as electromagnetic RF signals. Illustratively, the RF link can be an On-Off Keying (OOK) modulated 5 MHz RF link, although different forms of modulation and signal frequencies can be used in other examples.

Each of the power supplies 36, 50 provides power to various components of the first and second components 22, 24, respectively. The power supplies 36, 50 can be any suitable power supply, such as non-rechargeable or rechargeable batteries. In one example, one or more both of the power supplies 36, 50 are batteries that can be recharged wirelessly, such as through inductive charging. Generally, a wirelessly rechargeable battery facilitates complete subcutaneous implantation of a device to provide fully or at least partially implantable prostheses. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined or otherwise, associated with use of the prosthesis.

Further, the data storage 34, 48 may be any suitable volatile and/or non-volatile storage components. Further, the data storage 34, 48 may store computer-readable program instructions and perhaps additional data. In some embodiments, the data storage 34, 48 stores data and instructions used to perform at least part of the processes disclosed herein and/or at least part of the functionality of the systems described herein. Although the data storage 34, 48 in FIG. 1 are illustrated as separate blocks, in some embodiments, the data storage can be incorporated, for example, into the processor(s) 30, 44, respectively.

As mentioned above, the processor 30 is configured to convert the audible sounds 60 into encoded electronic signals, and the communication electronics 32 are configured to transmit the encoded electronic signals as the output signals 62 to the communication electronics 42. In particular, the processor 30 may utilize configuration settings, auditory processing algorithms, and a communication protocol to convert the audible sounds 60 into the encoded electronic signals that are transmitted as the output signals 62. One or more of the configuration settings, auditory processing algorithms, and communication protocol information can be stored in the data storage 34. Illustratively, the auditory processing algorithms may utilize one or more of speech algorithms, filter components, or audio compression techniques. The output signals 62 can also be used to supply power to one or more components of the second component 24. Generally, the encoded electronic signals themselves include power that can be supplied to the second component 24. Additional power signals can also be added to the encoded electronic signals to supply additional power to the second component 24.

The second component 24 can then apply the encoded electronic signals to the stimulation electronics 46 to allow a recipient to perceive the electronic signals as sound. Generally, the stimulation electronics 46 can include a transducer or actuator that provides auditory stimulation to the recipient through one or more of electrical nerve stimulation, audible sound production, or mechanical vibration of the cochlea, for example.

In the present example, the communication protocol defines how the encoded electronic signals are transmitted from the first component 22 to the second component 24. For example, the communication protocol can be an RF protocol that the first component applies after generating the encoded electronic signals, to define how the encoded electronic signals will be represented in a structured signal frame format of the output signals 62. In addition to the encoded electronic signals, the communication protocol can define how power signals are supplied over the structured signal frame format to provide a more continuous power flow to the second component 24 to charge the power supply 50, for example. Illustratively, the structured signal format can include output signal data frames for the encoded electronic signals and additional output signal power frames.

Once the encoded electronic signals and/or power signals are converted into the structured signal frame format using the communication protocol, the encoded electronic signals and/or power signals can be provided to the communication electronics 32, which can include an RF modulator. The RF modulator can then modulate the encoded electronic signals and/or power signals with a carrier signal, e.g., a 5 MHz carrier signal, and the modulated signals can then be transmitted over the RF link from the communication electronics 32 to the communication electronics 40. In various examples, the modulations can include OOK or frequency-shift keying (FSK) modulations based on RF frequencies between about 100 kHz and 50 MHz.

The second component 24 may then receive the output signals 62 via the communication electronics 42. In one example, the communication electronics 42 include a receiving coil and associated circuitry for receiving electromagnetic RF signals, such as the output signals 62. The processor 44 is configured to then decode the output signals 62 and extract the encoded electronic signals. And the processor 44 can then apply the encoded electronic signals and the included audio data to the recipient via the stimulation electronics 46. Further, when the output signals 62 include power signals, the communication electronics 42 are configured to apply the received output signals 62 to charge the power supply 50.

The data integrity of the output signals 62 (including the encoded electronic signals and audio data) received by the second component 24 is important so that a recipient of the device 20 can accurately perceive the audible sounds 60 when the encoded electronic signals are applied to the recipient by the stimulation electronics. Power efficiency of the device 20 is also important to prolong the operation of the device before the power supplies 36, 50 need to be recharged, for example. As will be described in more detail hereinafter, there are a variety of operational settings of the device 20 that can be implemented to help to ensure good data integrity. Some of these operational settings when implemented, however, can reduce power efficiency of the device 20. The present disclosure relates to testing of these operational settings to obtain a good balance between data integrity and power efficiency.

As described generally above, the communication electronics 32 can be configured to transmit data and power to the communication electronics 42. Likewise, the communication electronics 42 can be configured to transmit signals to the communication electronics 32, and the communication electronics 32 can be configured to receive signals from the second component 24 or other devices or components.

Referring back to the stimulation electronics 46 of FIG. 1, these electronics can take various forms depending on the type of hearing prosthesis. Illustratively, in embodiments where the hearing prosthesis 20 is a direct acoustic cochlear stimulation device, the microphone 28 is configured to receive the audible sounds 60, and the processor 30 is configured to encode the audible sounds (or other electronic sound information) into the output signals 62. In this example, the communication electronics 42 receive the output signals 62, and the processor 44 applies the output signals to the recipient's inner ear via the stimulation electronics 46. In that example, the stimulation electronics 46 includes or is otherwise connected to an auditory nerve stimulator to transmit sound to the recipient via direct mechanical stimulation.

For embodiments where the hearing prosthesis 20 is a bone conduction device, the microphone 28 and the processor 30 are configured to receive, analyze, and encode audible sounds 60 (or other electronic sound information) into the output signals 62. The communication electronics 42 receive the output signals 62, and the processor 44 applies the output signals to the bone conduction device recipient's skull via the stimulation electronics 46. In this embodiment, the stimulation electronics 46 may include an auditory vibrator to transmit sound to the recipient via direct bone vibrations, for example.

In addition, for embodiments where the hearing prosthesis 20 is an auditory brain stem implant, the microphone 28 and the processor 30 are configured to receive, analyze, and encode the audible sounds 60 (or other electronic sound information) into the output signals 62. The communication electronics 42 receive the output signals 62, and the processor 44 applies the output signals to the auditory brain stem implant recipient's auditory nerve via the stimulation electronics 46 that, in the present example, includes one or more electrodes.

In embodiments where the hearing prosthesis 20 is a cochlear implant, the microphone 28 and the processor 30 are configured to receive, analyze, and encode the external audible sounds 60 (or other electronic sound information) into the output signals 62. The communication electronics 42 receive the output signals 62, and the processor 44 applies the output signals to an implant recipient's cochlea via the stimulation electronics 46. In this example, the stimulation electronics 46 includes or is otherwise connected to an array of electrodes.

Further, in embodiments where the hearing prosthesis 20 is an acoustic hearing aid or a combination electric and acoustic bimodal hearing prosthesis, the microphone 28 and the processor 30 are configured to receive, analyze, and encode audible sounds 60 (or other electronic sound information) into output signals 62. The communication electronics 42 receive the output signals 62, and the processor 44 applies the output signals to a recipient's ear via the stimulation electronics 46 comprising a speaker, for example.

The device 20 illustrated in FIG. 1 further includes an external computing device 70 that is configured to be communicatively coupled to the first component 22 (and/or the second component 24) via a connection or link 72. The link 72 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, inductive or electromagnetic coupling or link, and the like.

In general, the computing device 70 and the link 72 are used to operate the device 20 in various modes. In a first example mode, the computing device 70 is used to develop and/or load a recipient's configuration data to the device 20, such as through the data interface 26. In another example mode, the computing device 70 is used to upload other program instructions and firmware upgrades, for example, to the device 20. In yet other example modes, the computing device 70 is used to deliver data (e.g., sound information or the predetermined orientation data) and/or power to the device 20 to operate the components thereof and/or to charge the power supplies 36, 50. Still further, the computing device 70 and the link 72 can be used to implement various other modes of operation of the prosthesis 20.

The computing device 70 can further include various additional components, such as a processor and a power source. Further, the computing device 70 can include a user interface or input/output devices, such as buttons, dials, a touch screen with a graphical user interface, and the like, that can be used to turn the one or more components of the device 20 on and off, adjust the volume, switch between one or more operating modes, adjust or fine tune the configuration data, etc.

Various modifications can be made to the device 20 illustrated in FIG. 1. For example, a user interface or input/output devices can be incorporated into the first component 22 or the second component 24. In another example, the second component 24 can include one or more microphones. Generally, the device 20 may include additional or fewer components arranged in any suitable manner. In some examples, the device 20 may include other components to process external audio signals, such as components that measure vibrations in the skull caused by audio signals and/or components that measure electrical outputs of portions of a person's hearing system in response to audio signals.

Figure 2:
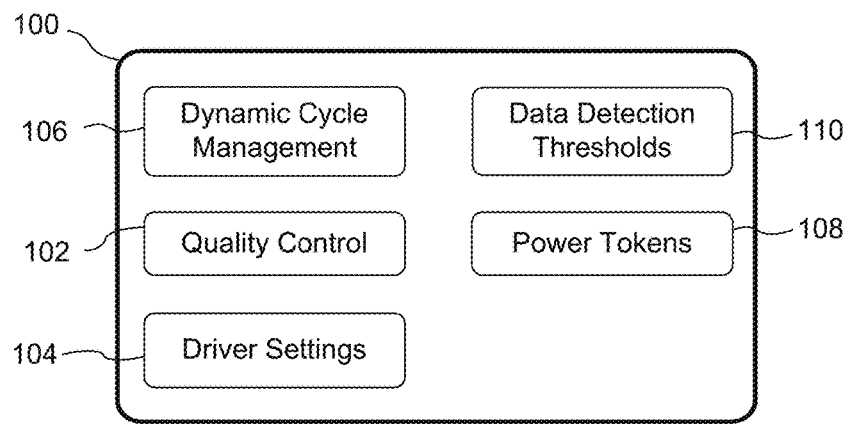
FIG. 2 is a block diagram illustrating various device settings according to an embodiment of the present disclosure.

Referring now to FIG. 2, in accordance with an embodiment of the present disclosure, the device 20 (e.g., the processor 30, driver circuitry of the communication electronics 32 and/or 42, and/or the processor 44) is configured to implement a combination or set of one or more operational settings 100 that may affect data integrity and/or power efficiency of the device. In the example of FIG. 2, these settings 100 include quality factor (Q) control mechanisms 102 to control a Q of the communication electronics 32, 42, driver settings 104 used to transmit the electronic signals, dynamic cycle modification (DCM) settings or tables 106 that are used to modify the electronic signals, power tokens 108 that may be added to the electronic signals, and data detection thresholds 110.

In one example, the Q-control mechanisms 102 include using different transceiver coils having different Qs. Generally, increasing the Q of the coils results in greater power efficiency by producing a larger magnetic field, but potentially reduces data integrity by narrowing signal bandwidth and making it more difficult to distinguish between "one" (high) and "zero" (low) data signals. In this example, the Q-control mechanisms 100 may include selectively using different transceiver coils as part of one or both of the communication electronics 32, 42. These different transceiver coils may include one transceiver coil that is printed on a circuit board and that may have a Q of about 30-40, and another transceiver coil that is a wire wound coil with a Q of about 50-60. In this example, the device may be configured to switch between the different transceiver coils for transmitting and receiving the output signals 62 in order to obtain a good balance between power efficiency and data integrity.

The Q-control mechanisms 102 may also include using dampening coils and/or resistors that can be selectively coupled to the communication electronics 32, 42 and, more particularly, coupled to the transceiver coils. Generally, a dampening coil may be selectively coupled in parallel with a transceiver coil. In one example, the device 20 is configured to couple the dampening coil to the transceiver coil to reduce the Q of the coil (dampen the coil) when a "zero" signal is transmitted, and to decouple the dampening coil when a "one" signal is transmitted. This selective dampening is intended to help prevent a "one" data signal cell from ringing into a "zero" data signal cell at signal transitions, which can reduce data integrity. As stated above, the Q-control mechanisms 102 may also include the device 20 selectively coupling dampening resistors to the transceiver coils. The device may be configured to selectively couple dampening resistors to the coils in order to dampen the coils and improve data integrity.

However, the coupling of damping coils/resistors reduces power efficiency by dissipating power in the damping coils/resistors. In the case of the dampening coil, by only coupling the dampening coil during a "zero" signal when there is no power transmission, the overall power efficiency penalty is less compared to always coupling the dampening coil. Yet, there is still a power efficiency penalty associated with coupling the dampening coil, since the timing of the dampening control may not be perfect and energy may be dissipated from the coils between "one" signals. Given this trade-off between power efficiency and data integrity when implementing dampening coils/resistors, the device may be configured to selectively implement these Q-control mechanisms in order to obtain a good balance between power efficiency and data integrity.

Figure 3:
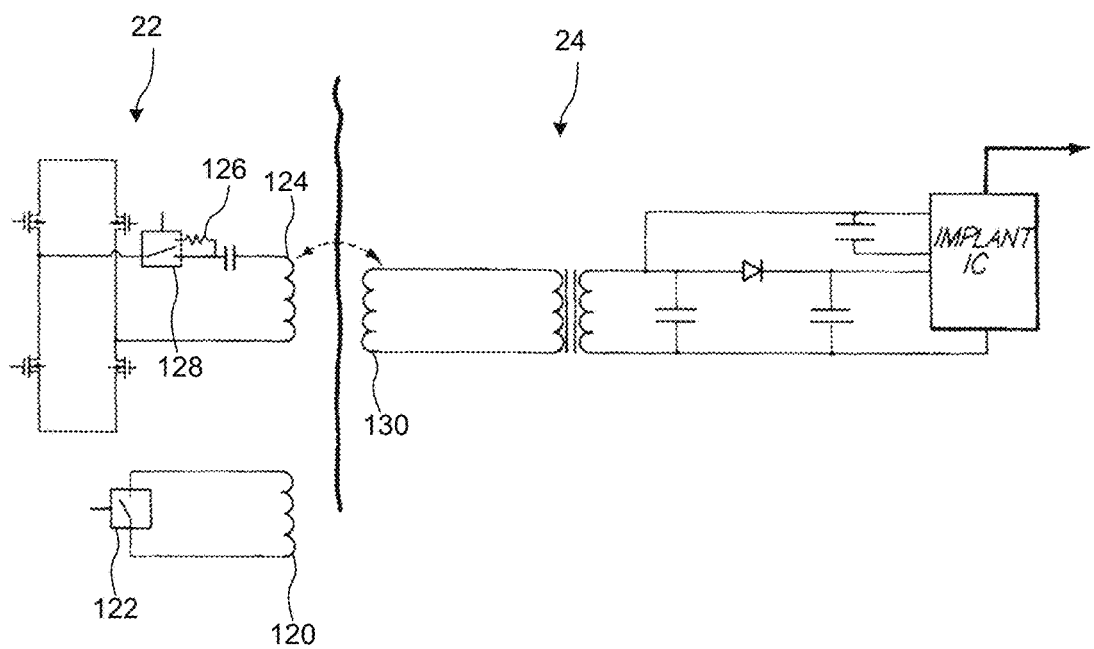
FIG. 3 is a circuit diagram illustrating an implementation of quality control settings in accordance with an embodiment of the present disclosure.

FIG. 3 illustrates an example of a dampening coil 120 that can be selectively coupled via a switch 122 to a coil 124 of the first component 22. FIG. 3 also illustrates a dampening resistor 126 that can be selectively coupled via a switch 128 to the coil 124 of the first component 22. The dampening resistor 126 can be selectively coupled in series (as shown) or in parallel with the coil 124 of the first component 22. Alternatively or in combination, a dampening coil and/or resistor can be selectively coupled (in series and/or in parallel) to a coil 130 of the second component 24. FIG. 3 also generally illustrates different coils 124, 130 that may have different Qs, and that may be selectively used to transmit/receive output signals.

In accordance with an embodiment of the present disclosure, the device 20 may also be configured to adjust driver settings 104 that are used to transmit electronic signals. In one example, the driver settings include selectively coupling one or more drivers in parallel that are used to deliver power to transceiver coils. Generally, increasing the number of drivers in parallel results in greater switching losses, but also results in lower conductive losses, which increases the Q and overall power efficiency. However, a higher Q also potentially reduces data integrity. Consequently, the device may be configured to adjust the number of parallel drivers in order to obtain a good balance between power efficiency and data integrity.

Figure 4:
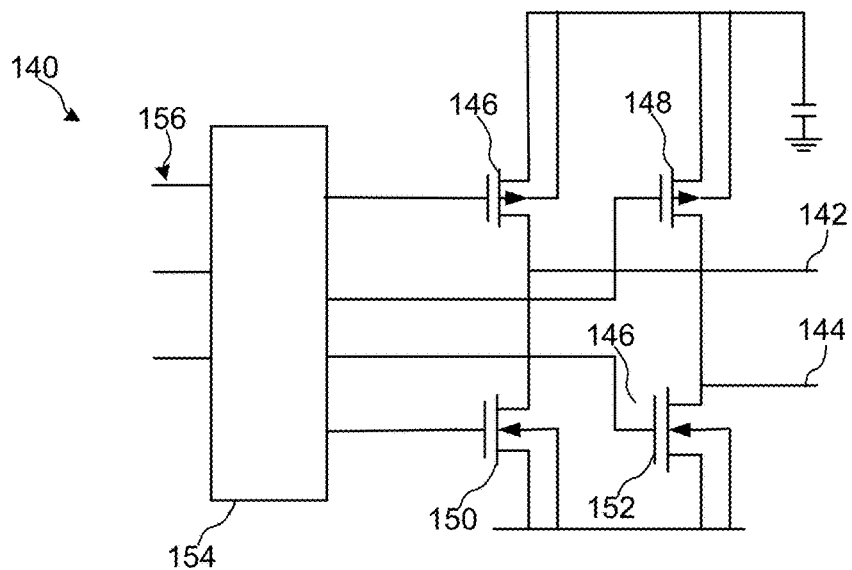
FIG. 4 is a circuit diagram illustrating driver circuitry in accordance with an embodiment of the present disclosure.

FIG. 4 illustrates an example driver circuit 140 that includes a first driver output 142 and a second driver output 144. Each driver output 142, 144 is provided by a push-pull stage with a pull-up P-channel transistor 146, 148 and a pull-down N-channel transistor 150, 152, respectively. Generally, gates of these transistors 146-152 are driven with separate non-overlapping signals, which helps to prevent the N-channel and P-channel transistors of each output 142, 144 from being fully or partially turned-on at the same time. The driver circuit 140 also includes a block 154 that represents additional logic and components for providing control signals to the transistors 146-152. For example, the block 154 can include a non-overlap circuit and pre-drivers to provide non-overlapping signals for driving the transistors. In addition, FIG. 4 illustrates one or more input lines 156 that are coupled to the block 154. These input lines can provide data and controls signals to the driver circuit 140. In other embodiments, the driver circuit 140 may include fewer or additional components, such as additional or fewer transistor half-bridges and driver outputs.

Referring back to the DCM settings or tables 104 mentioned above, the DCM tables are used to modify a length of each "one" and/or "zero" data signal based on a transmitted sequence. The use of the DCM tables 104 to modify the electronic signals can help to compensate for ringing between signal transitions and, thus, improve data integrity. There does not appear to be a significant power efficiency penalty for using DCM tables 104.

A single DCM table may be used for an entire population of recipients, however, such a DCM table may not improve data integrity for every recipient. In one embodiment of the present disclosure, the device 20 can test different DCM tables and select a particular DCM table to help to improve data integrity for a particular recipient. Additional details regarding DCM tables are disclosed in U.S. Patent Application Publication No. 2012/0213394 filed on Mar. 10, 2011, the contents of which are incorporated herein by reference.

In addition, the device 20 can selectively include power tokens or frames in the electrical signal. These power tokens may be dummy signals that are used to transmit power only and do not contain data. In one example, the device 20 can add these power tokens to the end of a data packet or frame. Adding power tokens may result in better data integrity. Further, the addition of power tokens also impacts power efficiency, because the power tokens affect a frame duty-cycle, and hence an effective load that is coupled to the communication electronics 32, 42. There may be a specific number of power tokens that helps to provide optimal power efficiency, and this number may be recipient-dependent. Consequently, in one example embodiment, the device 20 is configured to determine the number of power tokens that helps to provide optimal power efficiency for a particular recipient. The relationship between power efficiency, duty cycle, and effective load is described in more detail in U.S. Patent Application Publication No. 2013/0148828 filed on Dec. 9, 2011, the contents of which are incorporated by reference.

Further, the device 20 may also adjust signal level thresholds for detecting data in the transmitted electronic signals. For instance, the device 20 may adjust the data detecting thresholds 108 of the second component 24 for a particular recipient to improve data integrity. Alternatively or in combination, the device 20 may adjust the data detection thresholds of the second component based on statistics of the received electronic signal. Generally, adjusting data detection thresholds has little impact on power efficiency, but can be implemented to improve data integrity.

Figure 5:
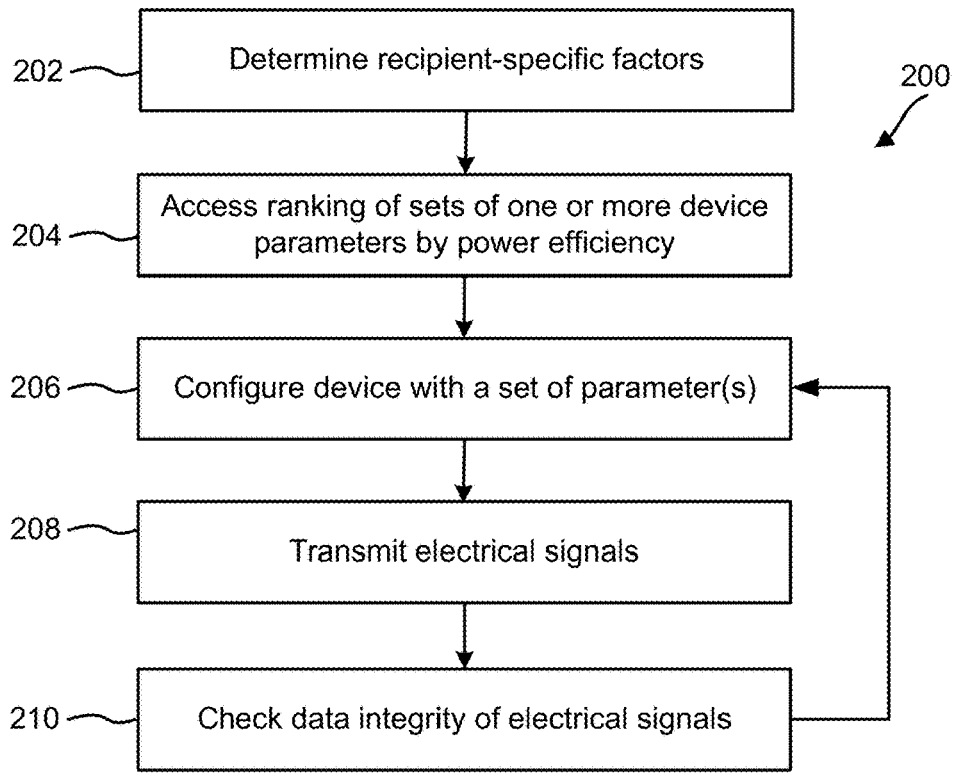
FIG. 5 is a flowchart showing a method for configuring a device in accordance with an embodiment of the present disclosure.

Referring now to FIG. 5 and with further reference to the description above, one example method 200 is illustrated for adjusting one or more settings of a device, such as the device 20 of FIG. 1, in order to improve power efficiency and data integrity of the device. Generally, the method 200 may include one or more operations, functions, or actions as illustrated by one or more of blocks 202-210. Although the blocks 202-210 are illustrated in sequential order, these blocks may also be performed concurrently and/or in a different order than illustrated. The method 200 may also include additional or fewer blocks, as needed or desired. For example, the various blocks 202-210 can be combined into fewer blocks, divided into additional blocks, and/or removed based upon a desired implementation.

The method 200 can be performed using the device 20 and components 22, 24 described above, for example. Further, the method 200 can be performed as part of a manufacturing process, as part of a fitting process for configuring the device for a recipient, and/or from time to time when the device is in use by the recipient.

In the method 200, at block 202, the device 20, the computing device 70, and/or a person (such as a clinician) determines one or more recipient-specific factors related to the device 20. These factors may include, for example, a skin flap thickness (SFT) over an implanted second component 24, electronic tolerances (such as, compliance voltage and electrode impedance), stimulation settings, and others.

In one embodiment, at block 202, the one or more recipient-specific factors may be determined while the device 20 is implanted in the recipient or otherwise configured for use by the recipient. In accordance with one example, the SFT is measured or estimated based on a magnitude of a back-link signal transmitted between the first and second components 22, 24. Generally, a relatively large back-link signal corresponds to a small SFT and a relatively small back-link signal corresponds to a larger SFT.

At block 204, the device 20 accesses data that ranks or lists sets of one or more device operational settings. More particularly, the data ranks or lists the sets of operational settings by power efficiency. In one embodiment, at block 204, the device 20 and/or the computing device 70 may store the data that ranks or lists the sets of device settings by power efficiency. Generally, this power efficiency ranking data can be determined by measuring the power efficiency using known power testing equipment and methods when implementing each individual device setting and/or by measuring the power efficiency when implementing combinations of device settings. These power efficiency measurements can be performed as part of a manufacturing process of the device, as part of a fitting process for configuring the device for a recipient, and/or periodically when the device is being used by the recipient.

At block 206, the device 20 implements a set of one or more settings for operating the device. These operational settings may relate to Q-control mechanisms (such as using coils having different Qs and using dampening coils/resistors), different driver settings (such as parallel driver settings), dynamic cycle modification (DCM) settings or tables, adjusting power tokens, and modifying data detection thresholds, for example. In accordance with one embodiment, at block 206, the device 20 uses the power efficiency data that was accessed at block 204 in order to implement a set of operational settings that has a relatively high power efficiency.

In one embodiment, at block 206, the device 20 may implement the set of operational settings in response to one or more of the determined recipient factors. In accordance with one embodiment of the present disclosure, a correlation has been identified between the SFT and the use of a dampening mechanism (such as dampening coils or resistors). More particularly, the use of a dampening mechanism has been determined to improve data integrity for low SFT below a given threshold, but reduces data integrity for higher SFT above the given threshold. In one example, the threshold SFT is about 6 mm. In this embodiment, if the determined SFT is below the threshold, the device may implement the dampening mechanism as one of the operational settings, and if the SFT is above the threshold, the device may not implement the dampening mechanism.

At block 208, the device 20 uses the implemented set of operational settings to generate and transmit electrical signals. For example, the first component 22 may use the implemented set of operational settings to transmit the output signals 62 to the second component 24. At block 210, the device 20 (e.g., the second component 24) analyzes data integrity of the transmitted electrical signals (e.g., the output signals 62). If the data integrity is acceptable, the device 20 may continue using the implemented set of operational settings. If the data integrity is not acceptable, at block 206, the device 20 may automatically implement a different set of one or more operational settings and the processes of blocks 208 and 210 may be repeated until the implemented set of operational settings provides acceptable data integrity. The device may select as the different set of operational settings, a set of operational settings that has a lower or perhaps the same power efficiency as the previously implemented set of operational settings. This iterative process of checking the data integrity associated with different sets of operational settings can be performed entirely by the device 20 with minimal interaction from a user (such as a clinician or the device recipient).

At block 208, the transmitted electrical signals can be predetermined test signals that the device analyzes at block 210 to check the data integrity of the transmitted electrical signals. In one example, the device 20 can transmit the electrical signals when operating in a telemetry or back-link mode that may be used specifically for testing data integrity and configuring device settings. The telemetry mode may be initiated by the first component 22 requesting telemetric feedback from the second component 24. The first component 22 may then transmit the electrical signals (and not other data/power signals) to the second component 24, which is configured to test the data integrity of the received signals.

In order to test the data integrity, the second component 24 may compare the received electrical signals with expected electrical signals in order to determine whether the data integrity of the transmitted signals is acceptable. In one example, the second component counts the number of packet errors between the received electrical signals and the expected electrical signals, and if the number of packet errors exceeds a threshold, the second component determines that the data integrity is not acceptable.

Figure 6:
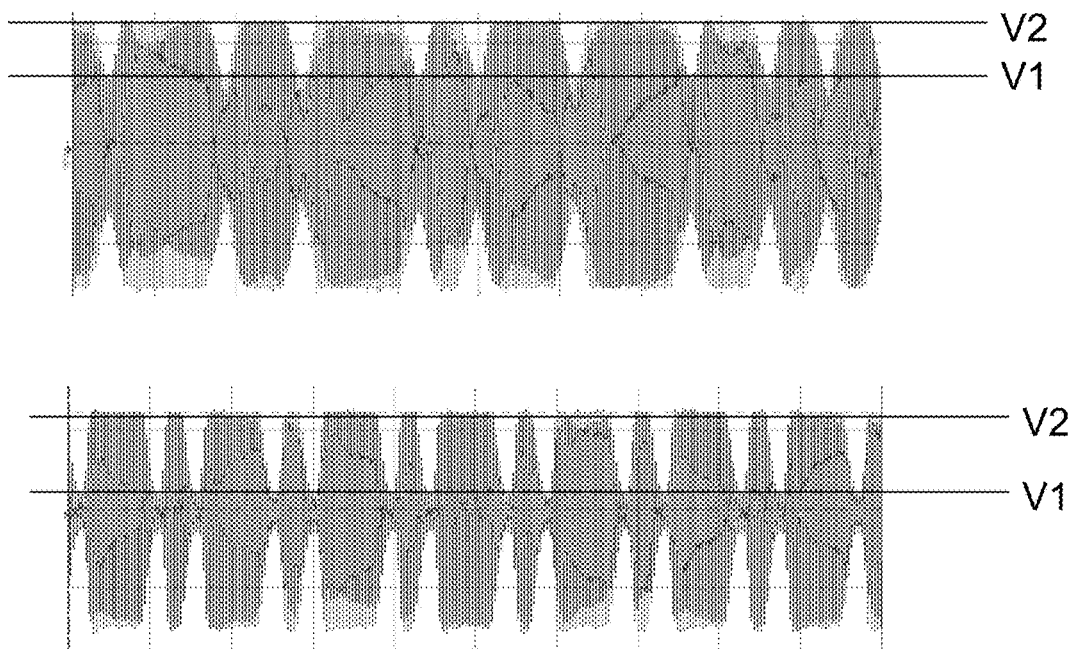
FIG. 6 illustrates modulation depths of two waveforms.

In addition or alternatively, the second component 24 may measure a modulation depth of the received electrical signals and may use the measured modulation depth as a metric for data integrity. Referring to FIG. 6, for example, the modulation depth can be defined as $(V2-V1)/V2$. A high modulation depth generally indicates that "zeroes" and "ones" are more easily distinguishable from each other and, thus, generally would result in acceptable data integrity. FIG. 6 illustrates an example of a low modulation depth (the upper waveform) and an example of a high modulation depth (the lower waveform).

If the second component 24 determines that the data integrity of the transmitted signals is acceptable, the second component can then transmit a corresponding data integrity signal back to the first component 22 to inform the first component that the data integrity was acceptable. If the second component 24 determines that the data integrity of the transmitted signal is not acceptable, and the second component may responsively transmit a corresponding data integrity signal back to the first component 24 to inform the first component that the data integrity was not acceptable. In another example, if the first component 24 does not receive the data integrity signal from the second component within a predetermined time period, the first component 24 is configured to then determine that the data integrity was not acceptable.

Each block 202-210 may represent a module, a segment, or a portion of program code, which includes one or more instructions executable by a processor for implementing specific logical functions or steps in the process. The program code may be stored on any type of computer-readable medium or storage device including a disk or hard drive, for example. The computer-readable medium may include non-transitory computer-readable medium, such as computer-readable media that stores data for short periods of time like register memory, processor cache, and Random Access Memory (RAM). The computer-readable medium may also include non-transitory media, such as secondary or persistent long-term storage, like read-only memory (ROM), optical or magnetic disks, compact-disc read-only memory (CD-ROM), etc. The computer-readable media may also include any other volatile or non-volatile storage systems. The computer-readable medium may be considered a computer-readable storage medium, for example, or a tangible storage device. In addition, one or more of the blocks 202-210 may represent circuitry that is wired to perform the specific logical functions of the method 200.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method, comprising:
at a medical device comprising first and second components:
configuring the medical device to operate in accordance with a first set of one or more operational settings;
generating, at the first component of the medical device, a first signal in accordance with a first set of one or more operational settings;
transmitting, by the first component, the first signal from the first component to the second component of the medical device;
determining that the first signal transmitted from the first component to the second component has an unacceptable data integrity; and
in response to the determining, automatically configuring the medical device to operate in accordance with a second set of one or more operational settings.

2. The method of claim 1, wherein the configuration of the medical device with the first set of one or more operational settings is associated with a power efficiency that is greater than a power efficiency of the configuration of the medical device with the second set of one or more operational settings.

3. The method of claim 1, wherein determining that the first signal has an unacceptable data integrity includes:
receiving, at the first component, a second signal generated and transmitted by the second component in response to receipt of the first signal,
wherein the second signal indicates that the data integrity of the first signal is below a threshold level.

4. The method of claim 1, wherein determining that the first signal has an unacceptable data integrity includes:
determining, at the first component, that no signals have been received from the second component within a predetermined time following transmission of the first signal.

5. The method of claim 1, further comprising:
generating, by the first component, a third signal in accordance with the second set of one or more operational settings;
transmitting, by the first component, the third signal from the first component to the second component;
determining, by the first component, whether the third signal has an acceptable data integrity;
if the third signal has an acceptable data integrity, then maintaining a configuration of the medical device with the second set of one or more operational settings; and
if third signal does not have an acceptable data integrity, then automatically configuring the medical device with a third set of one or more operational settings.

6. The method of claim 5, wherein the configuration of the medical device with the second set of one or more operational settings is associated with a power efficiency that is greater than a power efficiency of the configuration of the medical device with the third set of one or more operational settings.

7. The method of claim 1, wherein the second component is configured to be implanted in a recipient, and wherein transmitting the first signal from the first component to the second component of the medical device comprises:
transcutaneously transmitting the first signal from the first component to the second component.

8. The method of claim 1, wherein the operational settings include one or more of: quality-factor control mechanisms associated with communication electronics of the medical device, driver settings used to transmit signals, dynamic cycle modification settings, adjusting power tokens that are selectively included in signals, or data detection thresholds associated with detecting data in signals.

9. The method of claim 8, wherein determining the one or more factors related to the recipient includes determining a skin flap thickness ("SFT") over the implantable component of the medical device.

10. The method of claim 1, further comprising:
determining one or more factors related to a recipient of the medical device; and
selecting, by the medical device, the first set of one or more operational settings based on the determined one or more factors related to the recipient.

11. The method of claim 10, wherein the second component is configured to be implanted in a recipient, and wherein determining the one or more factors related to the recipient includes:

determining a skin flap thickness ("SFT") over the second component of the medical device.

12. The method of claim 1, wherein determining whether the first signal has an unacceptable data integrity includes:
performing, at the medical device, at least one of a modulation depth measurement of the first signal or a count of packet errors of the first signal.

13. The method of claim 1, further comprising:
accessing data that ranks a plurality of sets of one or more operational settings by power efficiency;
configuring the medical device with the first set of one or more operational settings based on the data; and
configuring the medical device with the second set of one or more operational settings in based on the data.

14. A external component of a medical device, comprising:
communication electronics;
at least one processor configured to:
implement a first set of one or more operational settings to generate a first signal and to use the first set of one or more operational settings and the communication electronics to transcutaneously transmit the first signal to an implantable component,
determining whether the first signal transmitted from the external component to the implantable component has an acceptable data integrity;
if the first signal has an acceptable data integrity, then maintaining a configuration of at least the external component to continue operation in accordance with the first set of one or more operational settings; and
if the first signal does not have an acceptable data integrity, then automatically reconfiguring at least the external component to operate in accordance with a second set of one or more operational settings.

15. The external component of claim 14, wherein the configuration of the external component with the first set of one or more operational settings is associated with a power efficiency that is greater than a power efficiency of the configuration of the external component with the second set of one or more operational settings.

16. The external component of claim 14, wherein to determine whether the first signal has an acceptable data integrity, the at least one processor is configured to:
receive, via the communication electronics, a second signal generated and transmitted by the implantable component in response to receipt of the first signal,
wherein the second signal indicates that the data integrity of the first signal is above or below a threshold level.

17. The external component of claim 14, wherein to determine whether the first signal has an acceptable data integrity, the at least one processor is configured to:
determine, at the external component, that no signals have been received from the implantable component within a predetermined time following transmission of the first signal.

18. The external component of claim 14, wherein the at least one processor is further configured to:
determine that the first signal has an unacceptable data integrity;
implement the second set of one or more operational settings to generate a third signal and to use the second set of one or more operational settings and the communication electronics to transcutaneously transmit the third signal to the implantable component;
determine whether the third signal has an acceptable data integrity;
if the third signal has an acceptable data integrity, maintaining a configuration of at least the external component with the second set of one or more operational settings; and
if the third signal does not have an acceptable data integrity, then automatically configuring at least the external component with a third set of one or more operational settings.

19. The external component of claim 18, wherein the configuration of at least the external component with the second set of one or more operational settings is associated with a power efficiency that is greater than a power efficiency of the configuration of at least the external component with the third set of one or more operational settings.

20. The external component of claim 18, wherein the operational settings include one or more of: quality-factor control mechanisms associated with communication electronics of the medical device, driver settings used to transmit signals, dynamic cycle modification settings, adjusting power tokens that are selectively included in signals, or data detection thresholds associated with detecting data in signals.

21. The external component of claim 18, wherein the at least one processor is configured to:
determine one or more factors related to a recipient of the medical device; and
select the first set of one or more operational settings in response to the determined one or more factors related to the recipient.

22. A method, comprising:
configuring a medical device with a first set of one or more operational settings;
generating, by the medical device, a first signal in accordance with a first set of one or more operational settings;
transmitting the first signal from a first component to a second component of the medical device:
determining, by the medical device, whether the first signal transmitted from the first component to the second component has an acceptable data integrity;
if the medical device determines that the first signal has an acceptable data integrity, maintaining a configuration of the medical device with the first set of one or more operational settings; and
if the medical device determines that the first signal does not have an acceptable data integrity, then automatically configuring the medical device with a second set of one or more operational settings, and
wherein the configuration of the medical device with the first set of one or more operational settings is associated with greater power efficiency than the configuration of the medical device with the second set of one or more operational settings.

23. The method of claim 22, wherein the medical device includes a first component and a separate second component, further wherein generating the first signal includes the first component generating the first signal, wherein the method further includes transmitting, by the first component, the first signal from the first component to the second component.

24. The method of claim 23, wherein determining that the first signal has an acceptable data integrity includes the first component receiving a second signal in response to the transmitted first signal, wherein the second signal is indicative of an acceptable data integrity of the transmitted first signal, and wherein the second signal being generated and transmitted by the second component, further wherein determining that the first signal does not have acceptable data integrity includes the first component not receiving the second signal.

25. The method of claim 24, further comprising:
if the first component does not receive the second signal in response to the transmitted first signal, then generating, by the first component, a third signal in accordance with the second set of one or more operational settings;
transmitting, by the first component, the third signal from the first component to the second component;
if the first component receives a fourth signal in response to the transmitted third signal, wherein the fourth signal is indicative of an acceptable data integrity of the transmitted third signal, and wherein the fourth signal being generated and transmitted by the second component, then maintaining the configuration of the medical device with the second set of one or more operational settings; and
if the first component does not receive the fourth signal in response to the transmitted third signal, then automatically configuring the medical device with a third set of one or more operational settings, and
wherein the configuration of the medical device with the second set of one or more operational settings is associated with greater power efficiency than the configuration of the medical device with the third set of one or more operational settings.

26. The method of claim 22, wherein the operational settings include one or more of quality-factor control mechanisms, driver settings, dynamic cycle modification settings, adjusting power tokens, or modifying data detection thresholds.

27. The method of claim 22, further comprising determining one or more factors related to a recipient of the medical device, and selecting, by the medical device, the first set of one or more operational settings based on the determined one or more factors related to the recipient.

28. The method of claim 27, wherein determining the one or more factors related to the recipient includes determining a skin flap thickness ("SFT") over a component of the medical device.

29. The method of claim 22, wherein determining whether the first signal has an acceptable data integrity includes the medical device performing at least one of a modulation depth measurement of the first signal or a count of packet errors of the first signal.

* * * * *